United States Patent
Kecskemethy et al.

(10) Patent No.: US 11,455,723 B2
(45) Date of Patent: Sep. 27, 2022

(54) SECOND READER SUGGESTION

(71) Applicant: Kheiron Medical Technologies Ltd, London (GB)

(72) Inventors: Peter Kecskemethy, London (GB); Tobias Rijken, London (GB); Edith Karpati, Budapest (HU); Michael O'Neill, London (GB); Andreas Heindl, London (GB); Joseph Elliot Yearsley, London (GB); Dimitrios Korkinof, London (GB); Galvin Khara, London (GB)

(73) Assignee: KHEIRON MEDICAL TECHNOLOGIES LTD, London (GB)

( * ) Notice: Subject to any disclaimer, the term of this patent is extended or adjusted under 35 U.S.C. 154(b) by 0 days.

(21) Appl. No.: 17/251,398

(22) PCT Filed: Jun. 14, 2019

(86) PCT No.: PCT/GB2019/051668
§ 371 (c)(1),
(2) Date: Dec. 11, 2020

(87) PCT Pub. No.: WO2019/239155
PCT Pub. Date: Dec. 19, 2019

(65) Prior Publication Data
US 2021/0313043 A1 Oct. 7, 2021

(30) Foreign Application Priority Data

Jun. 14, 2018 (GB) .................................. 1809796
Nov. 27, 2018 (GB) .................................. 1819329
Jan. 7, 2019 (GB) .................................. 1900212

(51) Int. Cl.
*G06T 7/00* (2017.01)
*G06T 7/11* (2017.01)
(Continued)

(52) U.S. Cl.
CPC ............ *G06T 7/0012* (2013.01); *A61B 6/502* (2013.01); *A61B 6/5205* (2013.01);
(Continued)

(58) Field of Classification Search
CPC ........ G16H 30/20; G16H 50/20; G16H 30/40; G16H 40/67; G06T 7/11; G06T 7/0012;
(Continued)

(56) References Cited

U.S. PATENT DOCUMENTS 5,768,406 A 6/1998 Abdel-Mottaleb
5,999,639 A * 12/1999 Rogers ..................... B25J 15/04
382/132

(Continued)

FOREIGN PATENT DOCUMENTS

GB 2579244 A8 6/2020
JP 2013-039230 A 2/2013
(Continued)

OTHER PUBLICATIONS

UK Intellectual Property Office; Search Report for GB1819329.2 dated May 28, 2019.
(Continued)

*Primary Examiner* — Nay A Maung
*Assistant Examiner* — Jose M Torres
(74) *Attorney, Agent, or Firm* — Finch & Maloney PLLC

(57) ABSTRACT

The present invention relates to deep learning implementations for medical imaging. More particularly, the present invention relates to a method and system for suggesting whether to obtain a second review after a first user has performed a manual review/analysis of a set of medical images from an initial medical screening.

Aspects and/or embodiments seek to provide a method and system for suggesting that a second radiologist reviews one or more cases/sets of medical images in response to a first
(Continued)

radiologist's review of the case of medical images, based on the use of computer-aided analysis (for example using deep learning) on each case/set of medical images and the first radiologist's review.

20 Claims, 10 Drawing Sheets

(51) Int. Cl.
| | |
|---|---|
| G06T 7/70 | (2017.01) |
| G16H 30/40 | (2018.01) |
| A61B 6/00 | (2006.01) |
| G06K 9/62 | (2022.01) |
| G06N 3/08 | (2006.01) |
| G16H 30/20 | (2018.01) |
| G16H 50/20 | (2018.01) |
| G06T 7/143 | (2017.01) |
| G16H 40/67 | (2018.01) |
| G06V 10/764 | (2022.01) |
| G06V 10/774 | (2022.01) |
| G06V 30/19 | (2022.01) |

(52) U.S. Cl.
CPC .......... *A61B 6/5217* (2013.01); *A61B 6/5235* (2013.01); *G06K 9/6256* (2013.01); *G06K 9/6267* (2013.01); *G06N 3/08* (2013.01); *G06T 7/11* (2017.01); *G06T 7/143* (2017.01); *G06T 7/70* (2017.01); *G06V 10/764* (2022.01); *G06V 10/774* (2022.01); *G06V 30/19147* (2022.01); *G06V 30/19173* (2022.01); *G16H 30/20* (2018.01); *G16H 30/40* (2018.01); *G16H 40/67* (2018.01); *G16H 50/20* (2018.01); *G06T 2207/10081* (2013.01); *G06T 2207/10088* (2013.01); *G06T 2207/10116* (2013.01); *G06T 2207/10132* (2013.01); *G06T 2207/20076* (2013.01); *G06T 2207/20081* (2013.01); *G06T 2207/20084* (2013.01); *G06T 2207/30068* (2013.01); *G06T 2207/30096* (2013.01); *G06V 2201/03* (2022.01)

(58) Field of Classification Search
CPC . G06T 2207/20081; G06T 2207/20084; G06T 2207/30096; G06T 7/143; G06T 7/70; G06T 2207/10081; G06T 2207/10088; G06T 2207/10116; G06T 2207/10132; G06T 2207/20076; G06T 2207/30068; A61B 5/7267; A61B 6/025; A61B 6/032; A61B 6/467; A61B 6/502; A61B 6/5205; A61B 6/5217; A61B 6/5235; A61B 6/54; A61B 8/0825; A61B 8/467; A61B 8/5223; G06K 9/6256; G06K 9/6267; G06N 3/08; G06V 10/764; G06V 10/774; G06V 30/19147; G06V 30/19173; G06V 2201/03
See application file for complete search history.

(56) References Cited

U.S. PATENT DOCUMENTS

| | | | |
|---|---|---|---|
| 6,058,322 A | 5/2000 | Nishikawa et al. | |
| 6,574,304 B1 | 6/2003 | Hsieh | |
| 7,490,085 B2 * | 2/2009 | Walker | G16H 30/40 |
| 10,223,610 B1 | 3/2019 | Akselrod-Ballin et al. | |
| 2004/0184644 A1 | 9/2004 | Leichter et al. | |
| 2004/0228509 A1 | 11/2004 | Holupka et al. | |
| 2005/0010445 A1 * | 1/2005 | Krishnan | G06T 7/0012 |
| | | | 705/2 |
| 2005/0049497 A1 | 3/2005 | Krishnan et al. | |
| 2006/0100507 A1 | 5/2006 | Mertelmeier | |
| 2006/0122467 A1 | 6/2006 | Harrington et al. | |
| 2006/0177125 A1 | 8/2006 | Chan et al. | |
| 2007/0183641 A1 | 8/2007 | Peters et al. | |
| 2008/0159613 A1 | 7/2008 | Luo et al. | |
| 2009/0041327 A1 | 2/2009 | Chen et al. | |
| 2009/0118640 A1 | 5/2009 | Miller et al. | |
| 2009/0274349 A1 * | 11/2009 | Cascio | G06T 7/11 |
| | | | 382/128 |
| 2010/0135562 A1 * | 6/2010 | Greenberg | G16H 30/20 |
| | | | 382/131 |
| 2010/0256459 A1 | 10/2010 | Miyasa et al. | |
| 2010/0256991 A1 * | 10/2010 | Ishikawa | G16H 30/20 |
| | | | 705/3 |
| 2012/0099771 A1 | 4/2012 | Lao | |
| 2013/0218045 A1 * | 8/2013 | Ironstone | A61B 5/4312 |
| | | | 600/547 |
| 2013/0236078 A1 | 9/2013 | Kobayashi et al. | |
| 2013/0322711 A1 | 12/2013 | Schultz et al. | |
| 2014/0018681 A1 | 1/2014 | Chang et al. | |
| 2016/0314579 A1 | 10/2016 | Ghouti et al. | |
| 2016/0361121 A1 | 12/2016 | Reicher et al. | |
| 2016/0364528 A1 * | 12/2016 | Reicher | G16H 50/20 |
| 2016/0364857 A1 | 12/2016 | Reicher et al. | |
| 2017/0200266 A1 | 7/2017 | Podilchuk et al. | |
| 2018/0033144 A1 * | 2/2018 | Risman | G16H 30/20 |
| 2019/0189263 A1 * | 6/2019 | Stoval, III | G16H 50/30 |
| 2019/0340763 A1 | 11/2019 | Laserson | |
| 2021/0035296 A1 | 2/2021 | Mahrooghy et al. | |
| 2021/0248744 A1 | 8/2021 | Rijken et al. | |
| 2021/0312618 A1 | 10/2021 | Kecskemethy et al. | |

FOREIGN PATENT DOCUMENTS

| | | |
|---|---|---|
| JP | 2013039230 A | 2/2013 |
| WO | 99/05503 A3 | 4/1999 |
| WO | 2005/001740 A2 | 1/2005 |
| WO | 2005/001742 A2 | 1/2005 |
| WO | 2005001742 A2 | 1/2005 |
| WO | 2016/057960 A1 | 4/2016 |

OTHER PUBLICATIONS

UK Intellectual Property Office; Search Report for GB1809796.4 dated Dec. 17, 2018.
Dezso Ribli et al. "Detecting and classifying lesions in mammograms with Deep Learning", Sci Rep 2018: 8: 4165, published online Mar. 15, 2018. Doi: 10.1038/s41598-018-22437-z.
Z Huo et al, "Computerized analysis of multiple -mammographic views: potential usefulness of special view mammograms in computer-aided diagnosis", IEEE Trans Med Imaging Dec. 2001; 20(12):1285-92, DOI: 10.1109/42.974923 (Abstract).
Yufeng Zheng et al. "Breast Cancer Screening Using Convolutional Neural Network and Follow-up Digital Mammography", Proceedings of spie, vol. 10669, May 14, 2018 (May 4, 2018), pp. 1066905-1066905, XP060105634, DOI: 10.1117/12.2304564.
Kisilev Pavel et al., "Medical Image Description Using Multi-task loss CNN", Sep. 27, 2016, Intelligent Virtual Agent.IVA 2015. LNCS: [Lecture Notes in Computer Science; Lect. Notes in Comuter], Springer, Berlin, Heidelberg, p. 9s)121-129, XP047410045, ISBN: 978-3-642-17318-9.
Written Opinion of the International Searching Authority, PCT/G82019/051667, dated 2020.
IPRP, PCT/GB2019/051667, dated May 10, 2020.
Written Opinion of the International Searching Authority, PCT/GB2019/051668, dated 2020.
IPRP, PCT/GB2019/051668, dated May 10, 2020.
Written Opinion of the International Searching Authority, PCT/GB2019/051666.
IPRP, PCT/GB2019/051666, dated May 10, 2020.
Intl Search Report PCT/GB2019/051667, dated Nov. 1, 2019.
Intl Search Report, PCT/GB2019/051668, dated Nov. 6, 2019.
Intl Search Report, PCT/GB2019/051666, dated Sep. 23, 2019.

(56) References Cited

OTHER PUBLICATIONS

Dezso Ribli et al. "Detecting and classifying lesions in mammograms with Deep Learning", Sci Rep 2018: 8: 4165, published online Mar. 15, 2018. Doi: 10.1038/s41598-018-22437.
WOSA, PCT/GB2019/051668, Year: 2020.
IPRP, PCT/GB2019/051668, dated Oct. 5, 2020.
Canadian Intellectual Property Office; Examiner's Requisition for Application No. 3,102,173 (PCT No. GB2019051667) dated Jun. 29, 2021.
Canadian Intellectual Property Office; Examiner's Requisition for Application No. 3, 102, 174 (PCT No. GB2019051668) dated Jul. 6, 2021.
Canadian Patent Application 3,102,170, PCT/GB2019/051666; Requisition by Examiner dated Jul. 27, 2021.
U.S. Appl. No. 17/251,354, office action dated Aug. 3, 2021.
K. He, G. Gkioxari, P. Dollár and R. Girshick, "Mask R-CNN," 2017 IEEE International Conference on Computer Vision (ICCV), 2017, pp. 2980-2988, doi: 10.1109/ICCV.2017.322.
Paul F. Jaeger et al "Retina U-Net: Embarrassingly Simple Exploitation of Segmentation Supervision for Medical Object Detection" (https://arxiv.org/pdf/1811.08661.pdf).
EP Patent Appln 197447782, "Communication Under Rule 71 (3) EPC", Intention to Grant.
EP Patent Appln 19744778.2, "Communicatoin Under Rule 71(3) EPC", Intention to Grant.
EP Patent Appln 19744777.4, "Communication Under Rule 71(3) EPC", Intention to Grant, dated Sep. 30, 2021.
Canadian Intellectual Property Office; Examiner's Requisition for Application No. 3,102,173, (PCT No. GB20190516670 dated Dec. 9, 2021. 6 pages.
Canadian Patent Application 3,102,170, PCT/GB2019/051666; Requisition by Examiner, dated Jan. 11, 2022. 5 pages.
Canadian Intellectual Property Office; Examiner's Requisition for Application No. 3,102,170, (PCT No. GB2019051666) dated Jan. 11, 2022. 5 pages.
He, "A Review on Automatic Mammographic Density and Parenchymal Segmentation," International Journal of Breast Cancer, vol. 2015, Article ID 276217, (2015). 31 pages.

* cited by examiner

SECOND READER SUGGESTION

CROSS REFERENCE TO RELATED APPLICATIONS

This application is a national stage patent application filed under 35 U.S.C. § 371 of PCT International patent application PCT/GB2019/051668, filed Jun. 14, 2019, and claiming priority to GB patent application 1809796.4, filed Jun. 14, 2018, GB patent application 1819329.2, filed Nov. 27, 2018 and GB patent application 1900212.0 filed Jan. 7, 2019, the entire contents of each of which are incorporate by reference.

FIELD

The present invention relates to deep learning implementations for medical imaging. More particularly, the present invention relates to a method and system for suggesting whether to obtain a second review after a first user has performed a manual review/analysis of a set of medical images from an initial medical screening.

BACKGROUND

Mammography is an advanced method of scanning human breast tissue which makes use of low dose X-rays to produce images of the internal structure of the human breast. The screening of these images, called mammograms, aids early detection and diagnoses of breast abnormalities and diseases. In order to ascertain a more accurate scan, mammogram machines usually have two plates that compress the breast to spread the tissue apart and help radiologists examine the mammogram.

Assessment by human radiologists is believed to be the most accurate method of image evaluation, and refers to the task performed by a radiologist, or similar professional, of inspecting medical scans, section by section, in order to produce a comprehensive analysis. However, considering that a mammogram is a representation of three-dimensional information projected onto a two-dimensional image plane, there is often superimposition of tissues in the 2D medical scan images (mammograms) being inspected. As a result, tissues that appear superimposed within the image of the breast can reduce the visibility of malignant abnormalities or sometimes even simulate the appearance of an abnormality (false positive). This makes the task of analysing a mammogram more challenging and can cause difficulty when it comes to accurately and precisely detecting abnormalities.

In some situations only a single radiologist can review and diagnose the set of images produced from each set of mammogram image data. It is therefore possible that sometimes the single radiologist will not accurately diagnose a patient based on their review of mammogram image data. While it is sometimes preferred to use two independent radiologists to review each patient's mammogram image data independently, this is not always possible logistically or economically.

SUMMARY OF INVENTION

Aspects and/or embodiments seek to provide a method and system for suggesting that a second radiologist reviews one or more cases/sets of medical images in response to a first radiologist's review of the case of medical images, based on the use of computer-aided analysis (for example using deep learning) on each case/set of medical images and the first radiologist's review.

According to a first aspect, there is provided a computer-aided method of analysing medical images, the method comprising the steps of: receiving one or more medical images; analysing said one or more medical images to determine one or more characteristics; generating output data based on the determined one or more characteristics; receiving input data from a user relating to manually determined characteristics of the one or more medical images; and determining the degree of similarity of the determined one or more characteristics and the manually determined characteristics; wherein the output data is indicative of a requirement to obtain one or more additional medical tests if the degree of similarity is below a predetermined threshold an output is produced to trigger a further analysis of the one or more medical images.

Radiologists do not demonstrate consistent accuracy due to the manual nature of the task, for example, making errors due to superimposed breast tissues in the mammogram and/or details too fine for the human eye to detect. By comparing the manually determined one or more characteristics with computer-determined characteristics for the same data, the method can trigger a second manual review of the data thus only ever make a single radiologist approach safer by triggering a second manual review if there is a significant mismatch between the user diagnosis and the computer-aided analysis of each set of medical images.

Optionally the method is performed in substantially real-time. This can allow the trigger for the second manual review promptly, thus allowing the method to integrate with existing medical workflows more easily as it doesn't cause significant delay.

Optionally, the method can trigger or recommend one or more additional medical tests comprise any or any combination of: a computerised tomography (CT) scan; an ultrasound scan; a magnetic resonance imaging (MRI) scan; a tomosynthesis scan; and/or a biopsy.

A further medical test can be suggested based on the analysis of the preliminary screening.

As an example, a more detailed tomosynthesis scan can be instantaneously recommended if the initial mammogram is unclear or features are superimposed or there might be a lesion worth investigating. In some cases, the analysis from the initial medical image may not require any further workup or medical tests. Optionally, the output data may also indicate a breast density or tissue classification type.

Optionally, the one or more medical images comprises one or more mammographic or X-ray scans.

In most medical screening programmes, X-ray or mammography is the first type of medical scan.

Optionally, the step of analysing and determining is performed using one or more trained machine learning models.

Trained machine learning models can analyse medical images far quicker than a human expert, and hence increase the number of medical images analysed overall. The accuracy is typically consistent when using a machine learning model. Thus a problem, for example the growth of a cancerous tumour, can be detected more quickly than waiting for a human expert to become available and hence treatment may begin earlier or an additional medical test may be requested sooner. The identification of regions of interest, which may include lesions, may therefore aid screening and clinical assessment of breast cancer among other medical issues. Earlier diagnosis and treatment can reduce psychological stress to a patient and also increase the chances of survival in the long term.

Optionally, the trained machine learning models comprise convolutional neural networks.

Convolutional networks are powerful tools inspired by biological neural processes, which can be trained to yield hierarchies of features and are particularly suited to image recognition. Convolutional layers apply a convolutional operation to an input and pass the results to a following layer. With training, convolutional networks can achieve expert-level accuracy or greater with regard to segmenting and localising anatomical and pathological regions in digital medical images such as mammograms.

Optionally, the step of analysing and determining comprises segmenting one or more anatomical regions. Optionally, the output data further comprises overlay data indicating a segmentation outline and/or a probability masks showing one or more locations of one or more segmented regions.

Providing a clear and accurate segmentation of regions can be very helpful when reviewing a medical image, such as a mammogram. This may be especially relevant if there is reason to suspect there is a medical issue with a patient, for example a swollen area which is larger than it was in previous scans. Such changes may be more easily detectable if the different regions are clearly segmented. In addition, the segmentation information can also be used to enrich the Picture Archiving Communication Systems (PACS) that radiology departments use in hospitals. With the inclusion of this segmentation data on PACS, it advantageously improves future methods of flagging up similar cases, whether the methods are semi-automated, entirely automated or performed manually.

Optionally, the step of analysing and determining comprises identifying tissue type and density category. Optionally, the required type of the one or more additional medical tests are dependent upon the density category determined based on the one or more medical images. Optionally, this step may jointly estimate tissue type and density category.

Correctly classifying the tissue type and density category can enable the method to recommend an appropriate additional medical test or specific workup.

Optionally, the step of analysing and determining comprises automatically identifying one or more anomalous regions in the medical image.

Optionally, the step of analysing and determining comprises identifying and distinguishing between a malignant lesion and/or a benign lesion and/or typical lesion.

Optionally, the output data further comprises overlay data indicating a probability mask for the one or more lesions.

Optionally, the step of analysing and determining comprises identifying architectural distortion.

Optionally, the one or more medical images and the one or more additional medical images comprise the use digital imaging and communications in medicine, DICOM, files.

As a DICOM file is conventionally used to store and share medical images, conforming to such a standard can allow for easier distribution and future analysis of the medical images and/or any overlays or other contributory data. The one or more binary masks may be stored as part of a DICOM image file, added to an image file, and/or otherwise stored and/or represented according to the DICOM standard or portion of the standard.

According to a further aspect, there is provided a system for analysing sets of medical images in substantially real-time, the system comprising: a medical imaging device; a picture archiving communication system, PACS; a user terminal operable 202 to input diagnosis metadata for each set of medical images; a processing unit 201 operable to analyse one or more of each set of medical images on the PACS to determine one or more characteristics and determine a degree of similarity of the determined one or more characteristics and the input diagnosis metadata; and an output viewer operable to display a requirement for output data generated based on the determined one or more characteristics, wherein the output data is indicative of a requirement to obtain one or more additional medical images or trigger a further analysis of the set of medical images if the degree of similarity is below a predetermined threshold.

Such a system may be installed in or near hospitals, or connected to hospitals via a digital network, to reduce waiting times for medical images to be analysed. Patients may therefore be spared stress from not knowing the results of a medical scan and receive a decision more quickly.

Optionally, the processing unit 201 is integrated with the medical imaging device (FIG. 2).

In this way, the medical scanner can be coupled with a processing unit to analyse medical images as soon as they are scanned.

Optionally, the processing unit 201 is located remotely and is accessible via a communications channel (FIG. 3).

In this configuration, the processing unit 201 can be deployed from a remote cloud system without need to replace and change existing scanning equipment (FIG. 4).

According to a further aspect, there is provided a system operable to perform the method according to any other aspect.

According to a further aspect, there is provided a computer program operable to perform the method according to any other aspect.

Through the use of a computer or other digital technology, examination of medical images may be performed with greater accuracy, speed, and/or reliability that relying on a human expert. Therefore, a greater number of medical images may be reviewed at one time thereby reducing backlogs for experts and further reducing errors made when the medical images themselves are actually reviewed.

BRIEF DESCRIPTION OF DRAWINGS

Embodiments will now be described, by way of example only and with reference to the accompanying drawings having like-reference numerals, in which.

SPECIFIC DESCRIPTION

Referring to FIGS. 1 to 4, an embodiment will now be described.

Figure 1:
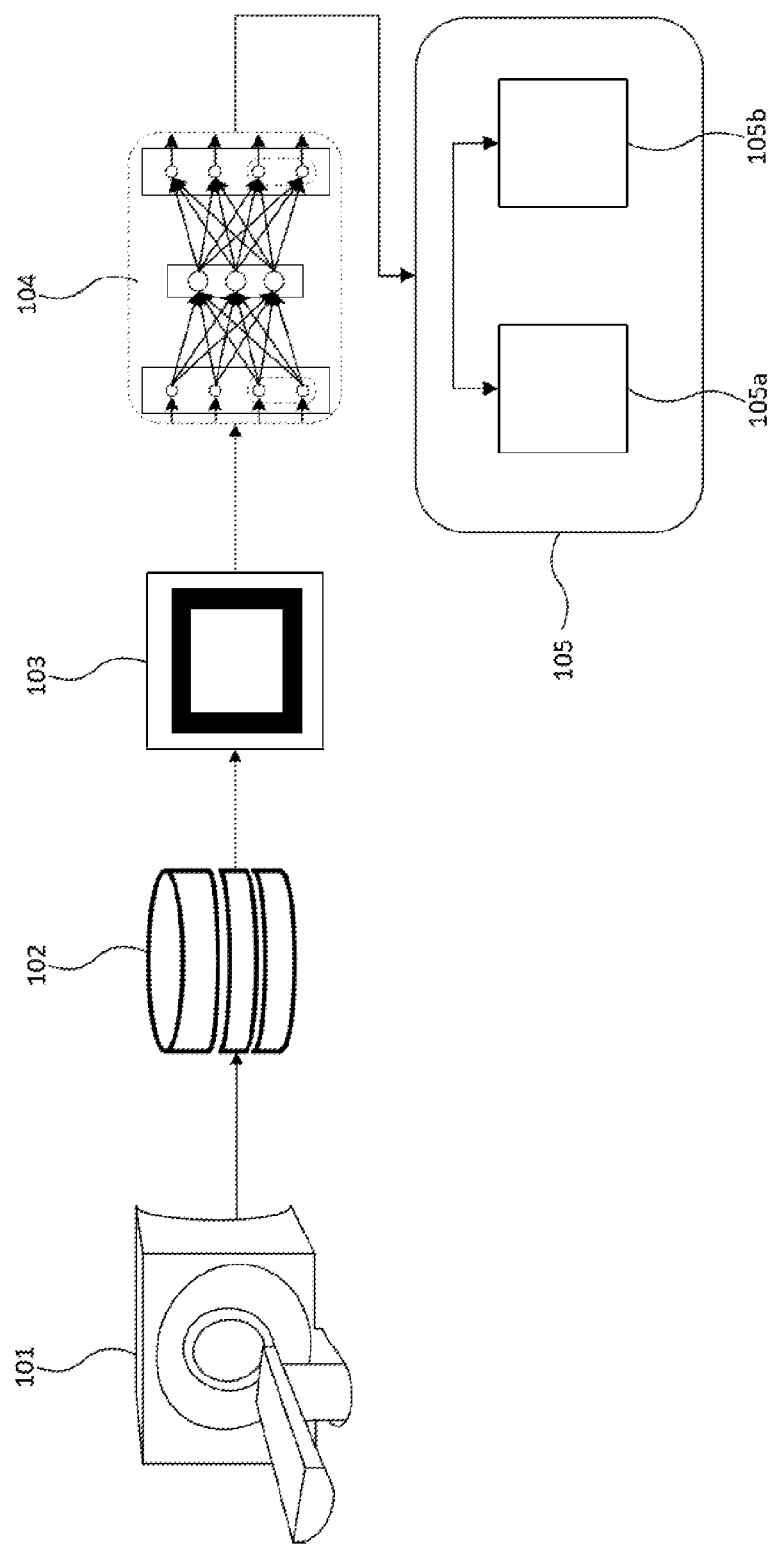
FIG. 1 shows a flow diagram of an embodiment.
Figure 2:
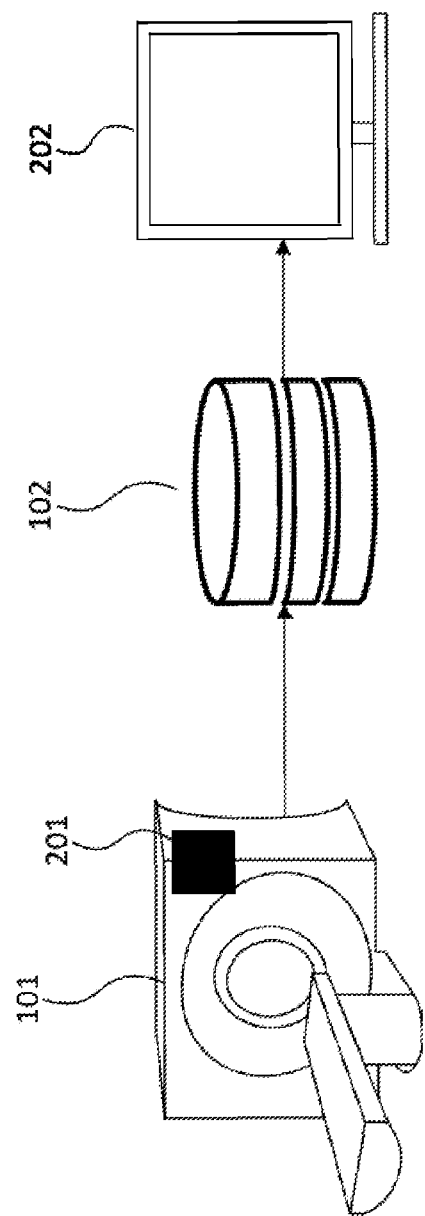
FIG. 2 depicts a first deployment (for example, within a medical scanning device)
Figure 3:
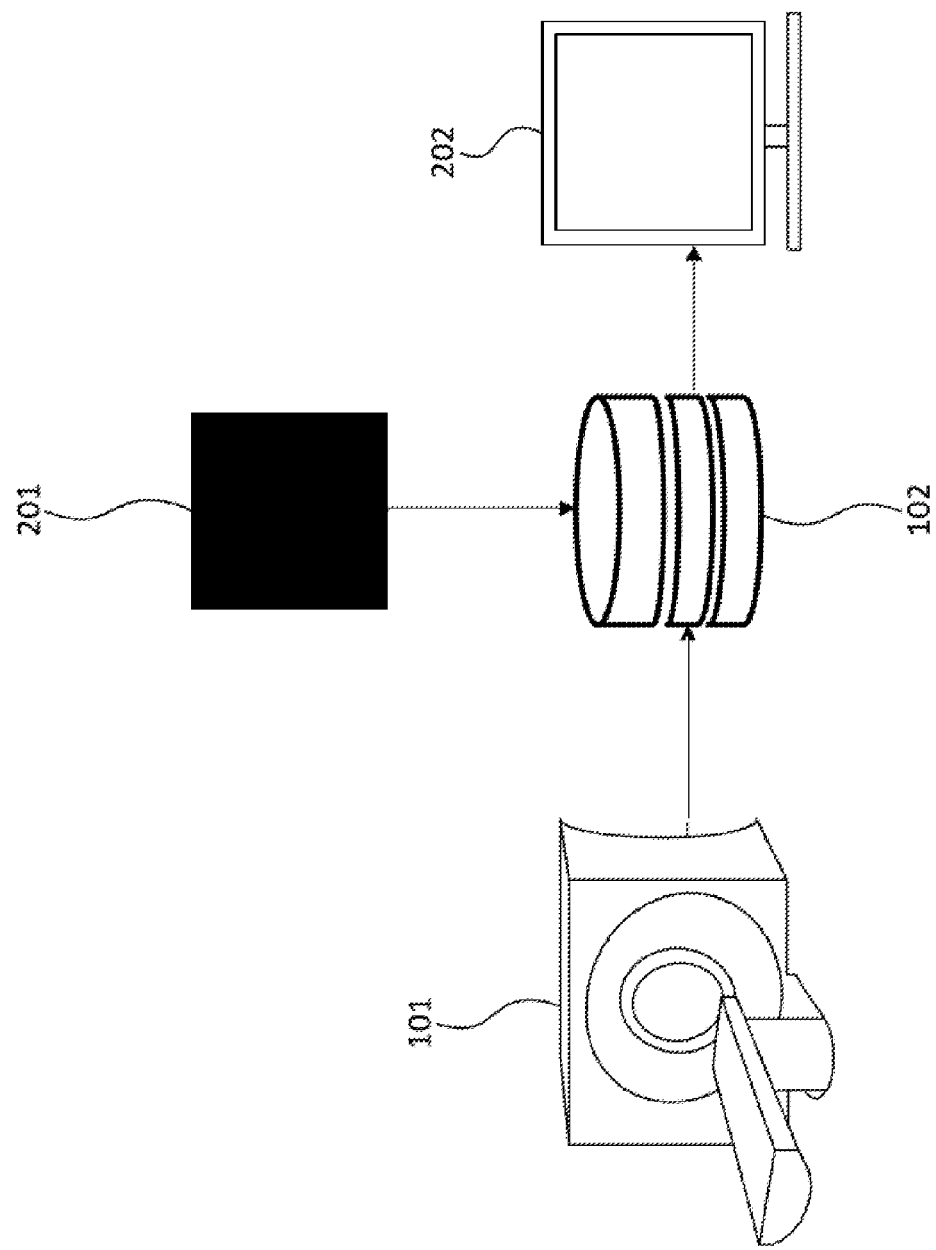
FIG. 3 depicts a second deployment (for example, on the premises of a medical facility)
Figure 4:
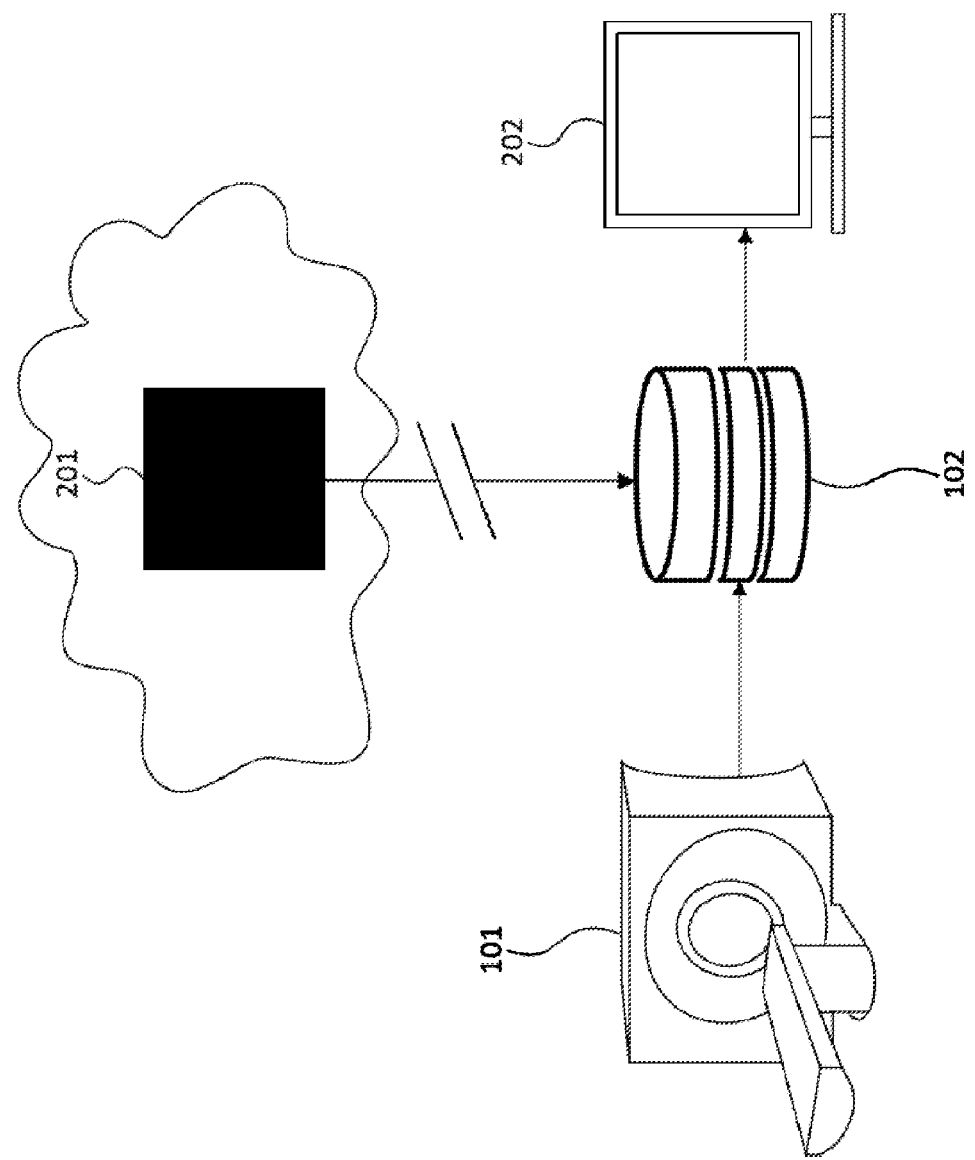
FIG. 4 depicts a third deployment (for example, using a cloud system)

As seen in FIG. 1, having performed a medical scan of a patient (such as a mammography) using a medical imaging scanner 101, the scanned images are collated in DICOM format, which is a file format commonly used to store medical images. The method uses pre-processed data that is stored on a Picture Archiving Communication Systems (PACS) 102 that radiology departments use in hospitals. The output of this method also enriches the PACS database to improve future applications of analysing mammographic images. Image data is extracted from the DICOM file and an image is generated. In an embodiment, a user terminal operable 202 to input diagnosis metadata for each set of medical images may be provided. In an embodiment, a processing unit 201 may be provided, wherein the processing unit is operable to analyse one or more of each set of medical images on the PACS to determine one or more characteristics and determine a degree of similarity of the determined one or more characteristics and the input diagnosis metadata.

The image then undergoes a pre-processing stage 103. The image is loaded onto a 4D tensor of size [1, width, height, 1]. The pre-processing stage may comprise windowing the image data to a predetermined windowing level. The windowing level defines the range of bit values considered in the image. Medical images are conventionally 16-bit images, wherein each pixel is represented as a 16-bit integer ranging from 0 to $2^{16}-1$, i.e. [0, 1, 2, . . . , 65535]. The information content is very high in these images, and generally comprises more information than what the human eye is capable of detecting. A set value for the windowing level is typically included within the DICOM file.

In some cases, it can be important to maintain image resolution. Often, conventional graphics processing unit (GPU) constraints require that the image is divided into a plurality of patches in order to maintain resolution. Each patch can then be provided to a Fully Convolutional Network (FCN). The larger the patch, the more context that can be provided but some precision may be lost. For example, in the case of a large image comprising a small tumour, if the FCN is instructed that somewhere in this patch there is a tumour, the network would need to learn how to find it first before it can be classified. In this embodiment patch sizes of 300×300 pixels are used, although larger and smaller patch sizes may be used.

A rescaling step may be included owing to above mentioned constraints of conventional hardware. Medical images are typically in the region of ~3500×2500 pixels. An FCN 100 applied to this image does not fit in conventional graphics processing unit (GPU) memory. The image can be rescaled to a larger or smaller size, or even not rescaled at all, and would allow the FCN to see a higher resolution and may pick up finer detail. However, this is unlikely to fit in GPU memory, and could cause the method to become considerably slower. By rescaling the image to a smaller size, it is more likely to be able to fit in a GPU memory, and allow the processes to run at a faster speed. The FCN may also generalise better owing to a smaller number of input parameters.

The method may be used to identify and detect lesions in the mammograms. The lesions which may be segmented may comprise one or more cancerous growths, masses, abscesses, lacerations, calcifications, and/or other irregularities within biological tissue.

The images are analysed by feeding them through a trained machine learning model, such as a Convolutional Neural Network 104. This embodiment utilises deep learning techniques to train and develop the convolution network. The model is trained on a dataset with known workups and, hence, directly establishes a relationship between the images received and the known workups to estimate a required workup. In particular, the output 105 of the machine learning model is a binary vector, where the indices represent various types of workup. For example, the workups may be any, or any combination of need no further action, an Ultrasound scan, a Tomosynthesis scan, an MRI scan and/or taking a Biopsy.

The dataset used for training the neural networks may also contain known density or tissue types. In that case, a multi-task learning approach can be taken to have the model also output density (A, B, C, D) or tissue type (1, 2, 3, 4, 5).

There are different types of patterns in breast tissue that affect the detectability of breast cancers. Thus, it is important to know what kind of pattern is present. There are five mammography parenchymal patterns known as "Tabar patterns", named after professor Laszlo Tabar who developed this classification.

The Tabar patterns (or classifications types) are based on a histologic-mammographic correlation with a three-dimensional, sub-gross (thick-slice) technique, and on the relative proportion of four "building blocks" (nodular densities, linear densities, homogeneous fibrous tissue, radiolucent fat tissue). The five classifications are as follows:

1. Balanced proportion of all components of breast tissue with a slight predominance of fibrous tissue
2. Predominance of fat tissue
3. Predominance of fat tissue with retro-areolar residual fibrous tissue
4. Predominantly nodular densities
5. Predominantly fibrous tissue (dense breast)

Classes 4 and 5 are considered high risk, meaning that it is difficult to detect cancers in the breast with those patterns, whereas classes 1, 2 and 3 are considered lower risk as it is easier to spot cancerous regions.

Some therapies may alter the pattern by increasing parenchymal density, as in hormone replacement therapy (HRT), or reducing it as in therapies with selective oestrogen-receptor modulators (SERM).

Similarly, breast density categories are classified by radiologists using the BI-RADS system. Again, this classification is used for quality control purposes. For example, it is very difficult to spot an anomaly in dense breasts. There are four categories in the BI-RADS system:

A. The breasts are almost entirely fatty
B. There are scattered areas of fibro-glandular density
C. The breasts are heterogeneously dense, which may obscure small masses
D. The breasts are extremely dense, which lowers the sensitivity of mammography Importantly, breast densities and tissue patterns are also known to have a mutual correlation to breast cancer development.

In some cases, the method can produce two types of output data. Whilst output data can relate to a suggested workup or additional medical tests 105*a*, the output data may also indicate the density or tissue classification 105*b*. The output data can indicate a binary output as to the requirement for further tests. Optionally, the output data can include data relating to how the binary output was reached, including any of; Tabar pattern; tissue classification types; breast density; nodular densities; linear densities; homogenous fibrous tissue; radiolucent fat tissue; BI-RADS category; a measure of superimposed features within the images; probability and/or confidence rating.

Mammography is a medical imaging modality widely used for breast cancer detection. Mammography makes use of "soft" X-rays to produce detailed images of the internal structure of the human breast—these images are called mammograms and this method is considered to be the gold standard in early detection of breast abnormalities which provide a valid diagnosis of a cancer in a curable phase.

Unfortunately, the procedure of analysing mammograms is often challenging. The density and tissue type of the breasts are highly varied and in turn present a high variety of visual features due to patient genetics. These background visual patterns can obscure the often tiny signs of malignancies which may then be easily overlooked by the human eye. Thus, the analyses of mammograms often lead to false-positive or false-negative diagnostic results which may cause missed treatment (in the case of false negatives) as well as unwanted psychological and sub-optimal downstream diagnostic and treatment consequences (in the case of false positives).

Most developed countries maintain a population-wide screening program, comprising a comprehensive system for calling in women of a certain age group (even if free of symptoms) to have regular breast screening. These screening programs require highly standardized protocols to be followed by experienced specialist trained doctors who can reliably analyse a large number of mammograms routinely. Most professional guidelines strongly suggest reading of each mammogram by two equally expert radiologists (also referred to as double-reading). Nowadays, when the number of available radiologists is insufficient and decreasing, the double-reading requirement is often impractical or impossible.

When analysing mammograms, the reliable identification of anatomical structures is important for visual evaluation and especially for analytic assessment of visual features based on their anatomic location and their relation to anatomic structures, which may have profound implications on the final diagnostic results. In the case that anatomic structures appear distorted they may also indicate the presence of possible malignancies.

Conventional X-ray is a medical imaging modality widely used for the detection of structural abnormalities related to the air containing structures and bones, as well as those diseases which have an impact on them. Conventional X-ray is the most widely used imaging method and makes use of "hard" X-rays to produce detailed images of the internal structure of the lungs and the skeleton. These images are called roentgenograms or simply X-rays.

Unfortunately, the procedure of analysing X-rays is often challenging, especially when analysing lung X-rays in order to detect infectious disease (e.g. TB) or lung cancer in early stage.

Cross-sectional medical imaging modalities are widely used for detection of structural or functional abnormalities and diseases which have a visually identifiable structural impact on the human internal organs. Generally, the images demonstrate the internal structures in multiple cross-sections of the body. The essence of the most widely used cross-sectional techniques are described below.

Computed tomography (CT) is a widely used imaging method and makes use of "hard" X-rays produced and detected by a specially rotating instrument and the resulted attenuation data (also referred to as raw data) are presented by a computed analytic software producing detailed images of the internal structure of the internal organs. The produced sets of images are called CT-scans which may constitute multiple series with different settings and different contrast agent phases to present the internal anatomical structures in cross sections perpendicular to the axis of the human body (or synthesized sections in other angles).

Magnetic Resonance Imaging (MRI) is an advanced diagnostic technique which makes use of the effect magnetic field impacts on movements of protons which are the utmost tiniest essential elements of every living tissue. In MRI machines the detectors are antennas and the signals are analysed by a computer creating detailed images if the internal structures in any section of the human body. MRI can add useful functional information based on signal intensity of generated by the moving protons.

However, the procedure of analysing any kind of cross-sectional images is often challenging, especially in the case of oncologic disease as the initial signs are often hidden and appearance of the affected areas are only minimally differed from the normal.

When analysing cross sectional scans, diagnosis is based on visual evaluation of anatomical structures. The reliable assessment, especially for analytic assessment, of visual appearance based on their anatomic location and their relation to anatomic structures, may have profound implications on final diagnostic results. In the case that anatomic structures appear distorted they may also indicate the presence of possible malignancies.

Generally, in the case of all diagnostic radiology methods (which include mammography, conventional X-ray, CT, MRI), the identification, localisation (registration), segmentation and classification of abnormalities and/or findings are important interlinked steps in the diagnostic workflow.

In the case of ordinary diagnostic workflows carried out by human radiologists, these steps may only be partially or sub-consciously performed but in the case of computer-based or computer-aided diagnoses and analyses the steps often need to be performed in a clear, concrete, descriptive and accurate manner.

Locality and classification may define and significantly influence diagnoses. Both locality and classification may be informed by segmentation in terms of the exact shape and extent of visual features (i.e. size and location of boundaries, distance from and relation to other features and/or anatomy). Segmentation may also provide important information regarding the change in status of disease (e.g. progression or recession).

Figure 5:
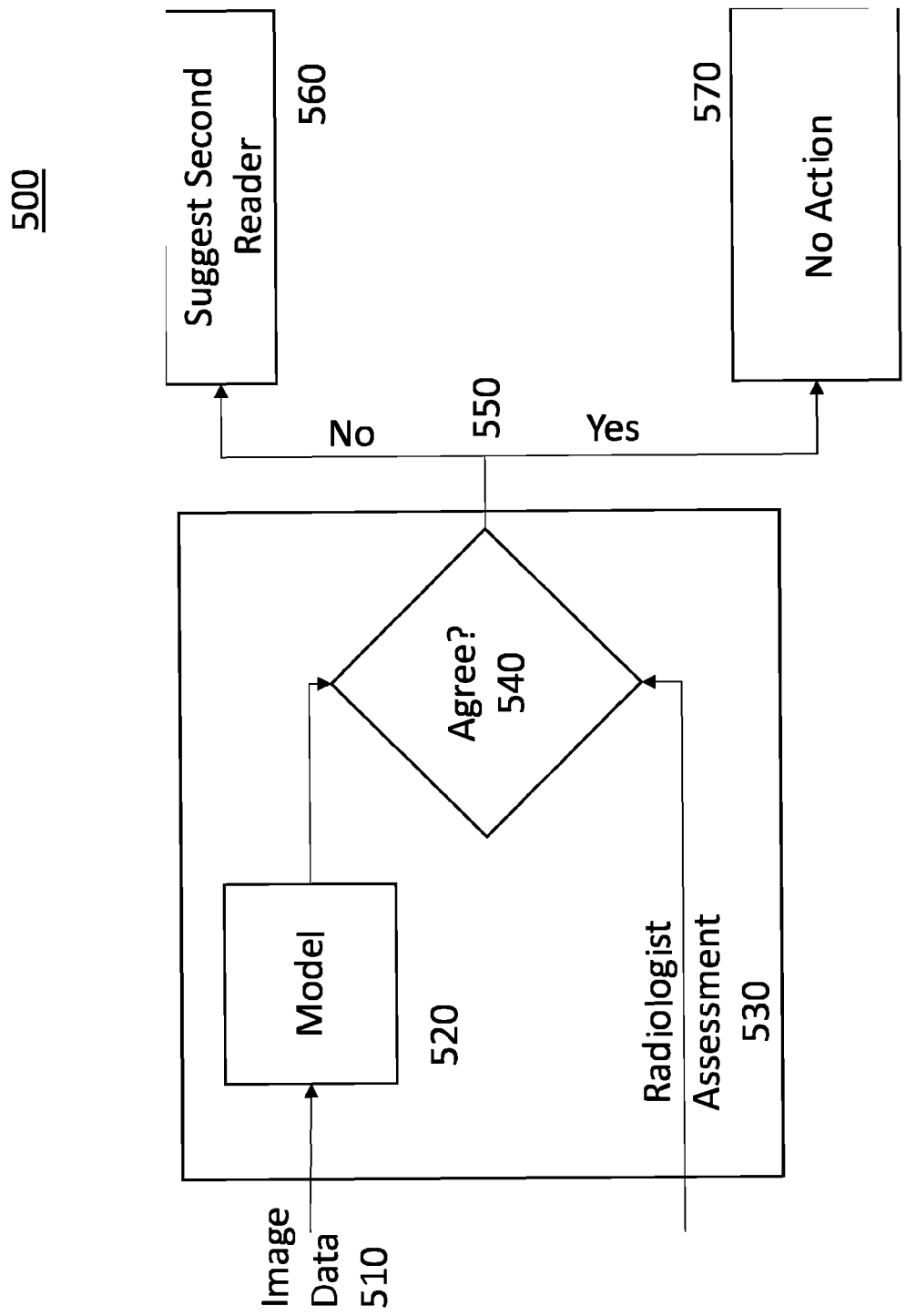
FIG. 5 illustrates a method of an embodiment.

Referring now to FIG. 5, there is shown a second reader suggestion method 500 according to an embodiment.

Mammography image data 510 is obtained for each patient and assessed by a radiologist as per standard clinical procedures. Once the assessment/diagnosis 530 has been completed by the radiologist, the mammography image data 510 is input into a model 520. The model 520 is arranged according to one of the embodiments described in this specification, for example according to the embodiment described in relation to FIGS. 1 to 4 or the embodiment described in accordance with FIGS. 6 to 10. The model 520 outputs an assessment of the input image data 510, for example highlighting portions of the image data 510 indicative of interest or concern to radiologists. The radiologist assessment 530 and the output of the model 520 are then compared 540 to determine if they do or don't overlap/agree. If there is not agreement between radiologist assessment 530 and the output of the model 520 then the output 550 triggers that a second reader is suggested 560, i.e. a second independent radiologist reviews the image data 510 and performs a second independent diagnosis. If the radiologist assessment 530 and the output of the model 520 agree, or overlap, then no further action needs to be taken 570.

The model 520 can be a machine learning (ML) model or system, for example a convolutional neural network.

The radiologist assessment 530 and the output of the model 520 can be determined to agree, or overlap, based on a threshold of similarity.

Alternatively, in addition this embodiment can also have other information input into the model 520 such as age of the patient and the model 520 configured to take this other information into account.

Another alternative is that, instead of a second independent radiologist being suggested to perform a second independent diagnosis, either the original radiologist can be alerted and it suggested that the original radiologist performs a second review; or a computer-aided-diagnosis is performed on the image data 510.

Figure 6:
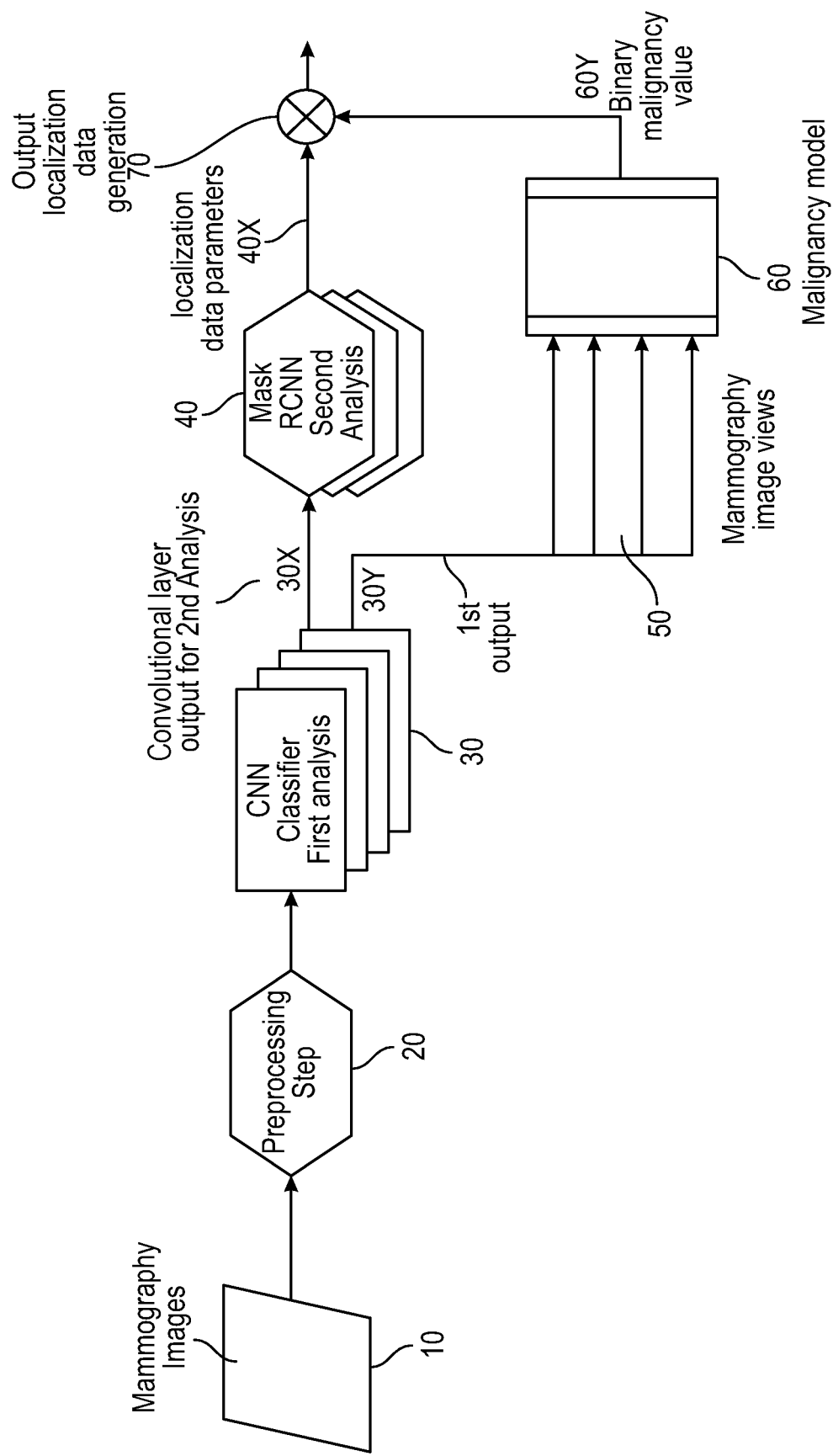
FIG. 6 illustrates a flowchart showing an outline of the method of an embodiment.

FIG. 6 depicts an example embodiment which will now be described in more detail below with reference to FIGS. 7 to 10 as appropriate.

Referring first to FIG. 6, there is shown a method for receiving input mammography images 10 and outputting a malignancy output, for example a yes/no binary output or a more detailed output showing regions of interest along with a binary output.

In a medical scan of a patient (mammography), the scanned images are collated in DICOM format, which is a file format commonly used to store medical images. The method uses pre-processed data 20 that is stored on a Picture Archiving Communication Systems (PACS) 10a (FIG. 7) that radiology departments use in hospitals. The output of this method also enriches the PACS database to improve future applications of analysing mammographic images.

In some instances, the images can be pre-processed using a variety of methods, including but not restricted to, windowing, resampling and normalisation. The input images may also undergo domain adaption and/or style transfer techniques to further improve the results.

The mammograms, pre-processed or not, are then fed into a convolutional neural network (CNN) classifier 30 which has been trained to analyse the images and assess whether the image shows a malignant lesion. In some embodiments, there is use of more than one trained CNN to complete this task. Conventional methods of detecting malignant lesions in a mammogram may also be used. Alternatively, other machine learning implementations may be used in place of a convolutional neural network.

In order for a CNN to operate as a malignancy model the network first needs to be trained. Similar to the pre-processing methods mentioned above, input images for the purpose of training the network may undergo windowing, resampling, normalisation, etc., before the images are used. In some instances, the images used to train the network are either provided or sized to up to 4000×4000 pixels.

As the images are fed through the CNN, a number of stacked mathematical operations are performed. In doing so, the CNN applies variable tensors to the previous layer such that a malignant or not score is produced as a result of these operations. We then update the variables based on the gradient of the cost function (cross-entropy) making use of the chainrule to work out the gradient updates to apply. In this way, multiple CNNs can be trained to be used with the described aspects/embodiments.

Additionally, the training of the CNNs may include concatenating a previous image taken of the same mammographic view and run it through the networks together with the current image being fed into the network. This enables the fine tuning of the final few layers of the CNN such that they can account for multiple images.

Figure 7:
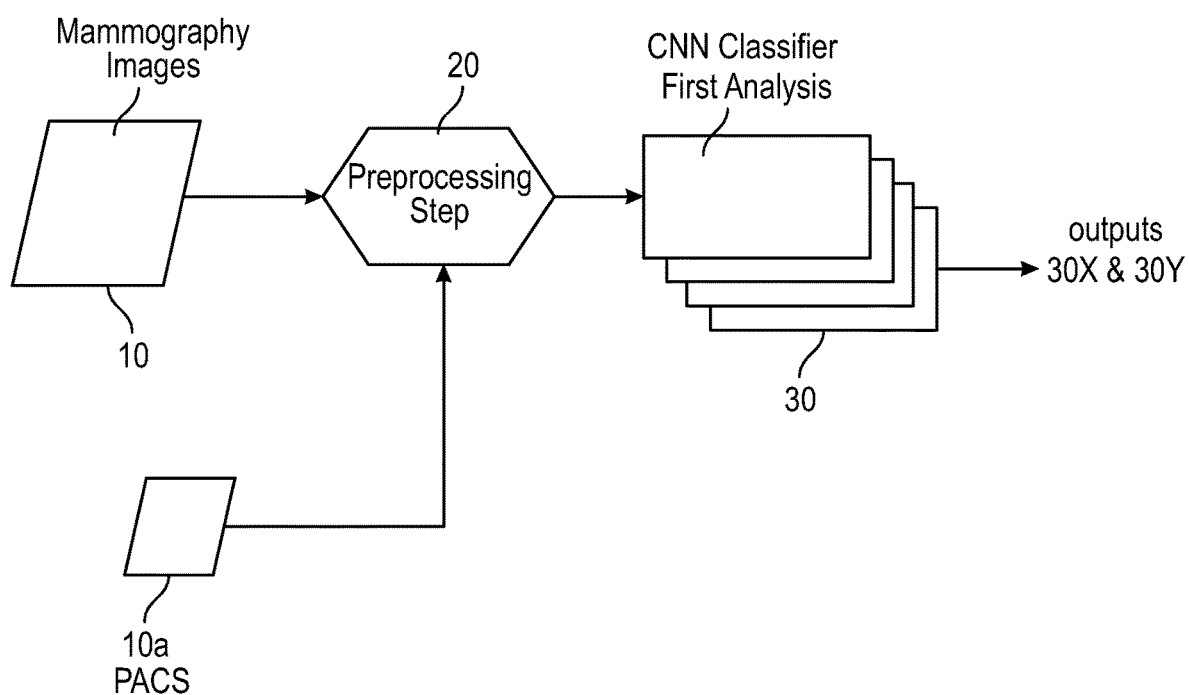
FIG. 7 illustrates the portion of the flowchart of FIG. 6 focussed on providing a malignancy output based on the input image and the pre-trained malignancy detection neural network, optionally showing the pre-processing that can be applied to the input image.
Figure 8:
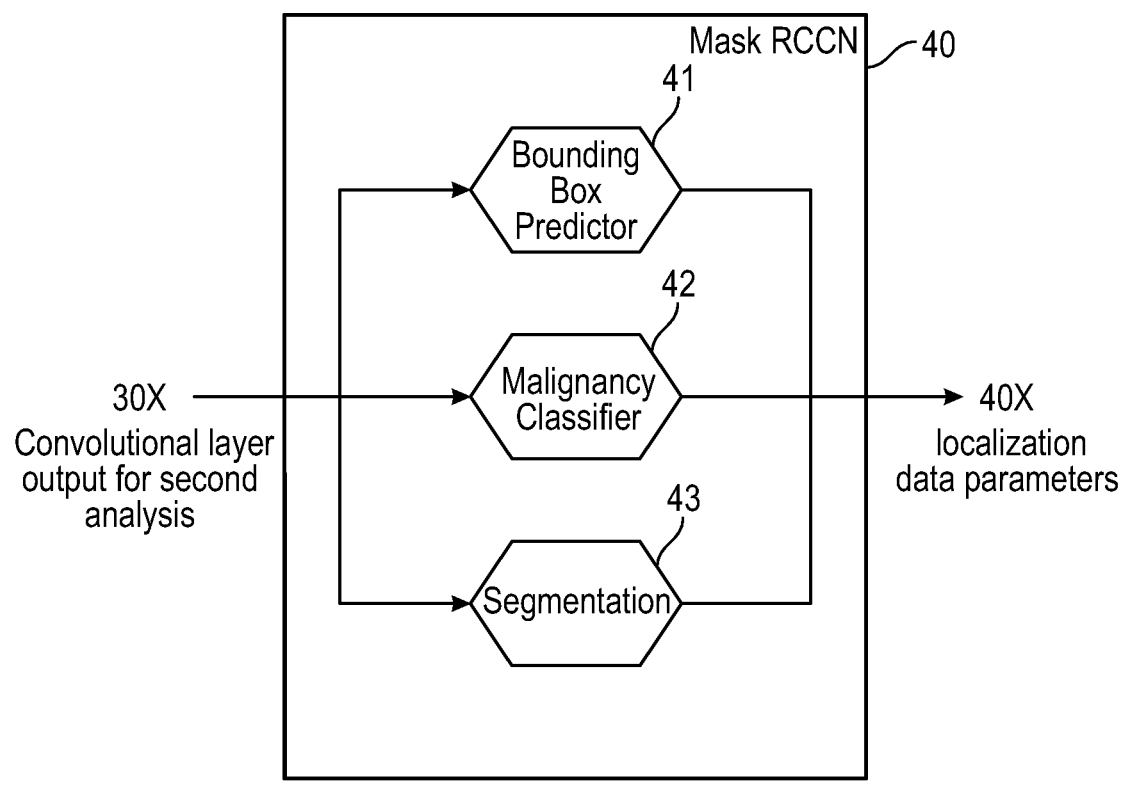
FIG. 8 illustrates the Mask R-CNN of the embodiment of FIG. 6 in more detail.

Once the malignancy model(s) are trained, the network and its weights are frozen. In an embodiment, the CNN classifier 30 provides outputs to two further processing steps, marked 30X and 30Y (FIGS. 6 and 7). One of the convolutional layer's outputs (30X) fed into mask heads from a Mask regional convolutional neural network (R-CNN) 40. An exemplary Mask R-CNN is illustrated in FIG. 8. These heads include a bounding box predictor 41, where the bounding boxes can be used to cut out a part of the original image.

In addition to, or on top of the cut-out patch, a malignant classifier 42 and segmentation 43 heads are placed. As with the malignancy model, any conventional bounding box, malignancy classifier or segmentation models can be used with this system. In "Mask R-CNN," 2017 IEEE International Conference on Computer Vision (ICCV), 2017, pp. 2980-2988, doi: 10.1109/ICCV.2017.322, Kaiming He, et al. describes a traditional R-CNN that can be used in at least some embodiments, which is incorporated by reference.

There are various methods of training the R-CNNs. Firstly, connecting the malignancy model to the Mask R-CNN the Mask R-CNN heads can be trained at the same time as the whole image malignancy model. Secondly, it is also possible to train the Mask R-CNN without freezing the malignancy model network. Finally, the Mask R-CNN heads may be trained with multiple malignancy models. Thus, the method of training the Mask R-CNN heads is not restricted to a certain type, which enables the approach to be tailored for specific uses.

Once the neural networks are trained, during use, or at inference time, the malignancy model is frozen based on the training data.

A second output 30Y from the CNN classifier may be a set of predetermined images 50 (FIG. 6). As an example, during run time, the system of the embodiment receives four types of mammography images (FIG. 9): left cranial caudal view (L-CC) 51, right cranial caudal view (R-CC) 53, left medio-lateraloblique (L-MLO) 52 and a right media-lateral-oblique (R-MLO) 54. This combination of images is known to be referred to as a case. Upon passing though the malignancy model 60 or models, the system of the embodiment produces an entire case of outputs. These outputs are then averaged to generate a single output 60Y.

Figure 9:
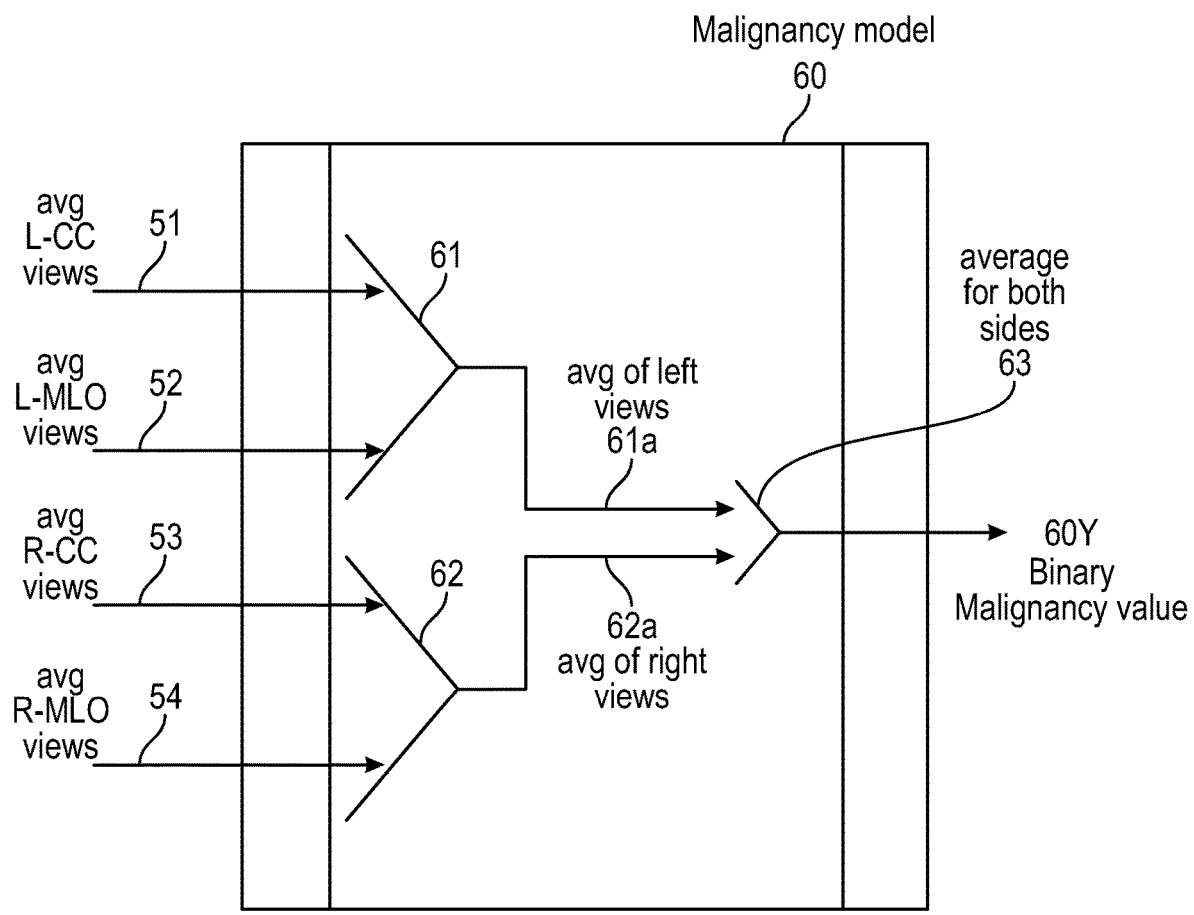
FIG. 9 illustrates the portion of the flowchart of FIG. 6 showing the process of the mean and max operations performed by the embodiment.

As seen in FIG. 9, 51 represents an average score of all left cranial caudal views, 52 represents an average score of all left medio-lateral-oblique (L-MLO) views, 53 represents an average score of all right cranial caudal (R-CC) views and 54 represents an average score of all right medio-lateral-oblique (R-MLO) views. As depicted by 61a and 62a, the system of the embodiment then calculates a mean of the respective left side views 61 and right side views 62. This results in a malignancy output for each side. A max operation 63 is then performed for the average malignancy outputs for each side.

Although not depicted in the Figures, in the described embodiment the method then thresholds this result with a predetermined threshold which gives a binary malignant or not score 60Y.

Figure 10:
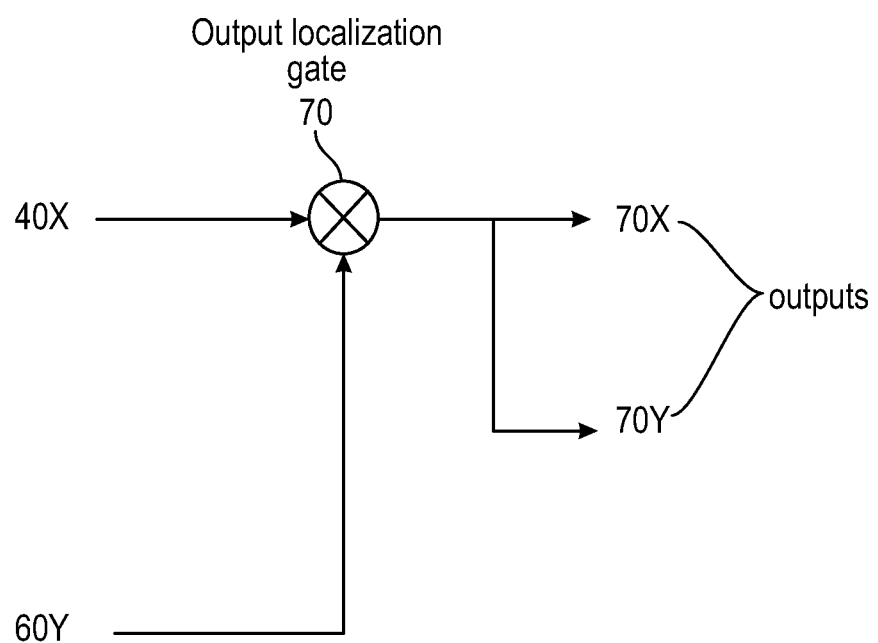
FIG. 10 illustrates how the final output of the embodiment of FIG. 6 is determined.

Finally, with reference to FIG. 10, the score 60Y is used to gate whether or not to show the Mask RCNN segmentations or bounding boxes 40X. Gate 70 is biased by score 60Y. In this way, instead of showing all potential lesions detected by the Mask R: CNN alone, which may lead to numerous false-positives, the resulting Mask R-CNN outputs (e.g., 70X and 70Y) are only shown if the binary malignant score is positive, i.e. indicating malignancy. When 60Y does not indicate the case to be malignant, the Mask R-CNN outputs are ignored and no localisation data is produced as an output of the system.

In some cases, the Mask RCNN results can be ensembled by interpolating between bounding box coordinates (of shape [N, M, x1, x2, y1, y2] where N represents the number of models and M the maximum number of bounding boxes) which have a sufficient intersection over union (IOU), which is predetermined. Any bounding box which does not have a sufficient IOU with the others are removed from consideration. With the resulting bounding boxes, the raw segmentation masks are then averaged before thresholding with a predetermined threshold, and also averaging the lesion scores for all of the sufficient bounding boxes.

These operations result in a final set of bounding boxes of shape [1, M, x1, x2, y1, y2] along with a segmentation mask of shape [1, H, W] and lesion scores of shape [1, M]. A better way is to use weighted box clustering (WBC) which is described by Paul F. Jaeger et al in "Retina U-Net: Embarrassingly Simple Exploitation of Segmentation Supervision for Medical Object Detection" (https://arxiv.org/pdf/1811.08661.pdf), which is incorporated by reference.

As aforementioned, double reading is the gold standard in breast cancer screening with mammography. In this scenario, two radiologists will report on a case. Arbitration will occur when the two readers are not in agreement about whether to recall a patient for further screening tests.

In the present embodiment, the described system is able to operate as an independent second reader so can assess whether a first radiologist diagnosis has identified all detected possible irregularities, abnormalities and/or malignant features in a set of medical images of a patient when provided with the diagnosis of the first radiologist and optionally some further information about each patient such as age (among other data). In the past, computer aided diagnosis systems were not able to act as such due to a high false positive rate. Similar to a human radiologist, the described system of the embodiment can have a low false positive rate which means it can be used in at least the following two ways:
1. As a truly independent second reader: a first (human) radiologist looks at the case and the present system independently assesses the case. If the two disagree, the system of the embodiment shows the outlines for lesions of interest for the human radiologist to consider, and if they agree, the radiologist does not see the outputs of the system; or
2. As a non-independent second reader where the human radiologist and the system of the embodiment both analyse the case—in that the human radiologist is supported by the system of the embodiment. The radiologist can click to see the results generated by the system of the embodiment whenever they want.
3. A verification tool once a first radiologist has performed a manual review and diagnosis of a set of images for a patient, provided that the tool is provided with both the set of images and the diagnosis information from the radiologist. If the diagnosis diverges from what the tool would expect a radiologist to diagnose in the set of images (and optionally based on the further data too, such as for example the age of the patient), then the tool can suggest that a second radiologist performs an independent review of the set of images and make a second diagnosis.

Many approaches that mimic the techniques used by human radiologists can be incorporated in the system in some embodiments, such as using a previous image as a reference to look for any changes since the last scan and also a mean then max operator to mimic the way human radiologists trade off calling back a case.

Machine learning is the field of study where a computer or computers learn to perform classes of tasks using the feedback generated from the experience or data gathered that the machine learning process acquires during computer performance of those tasks.

Typically, machine learning can be broadly classed as supervised and unsupervised approaches, although there are particular approaches such as reinforcement learning and semi-supervised learning which have special rules, techniques and/or approaches.

Supervised machine learning is concerned with a computer learning one or more rules or functions to map between example inputs and desired outputs as predetermined by an operator or programmer, usually where a data set containing the inputs is labelled.

Unsupervised learning is concerned with determining a structure for input data, for example when performing pattern recognition, and typically uses unlabelled data sets. Reinforcement learning is concerned with enabling a computer or computers to interact with a dynamic environment, for example when playing a game or driving a vehicle.

Various hybrids of these categories are possible, such as "semi-supervised" machine learning where a training data set has only been partially labelled. For unsupervised machine learning, there is a range of possible applications such as, for example, the application of computer vision techniques to image processing or video enhancement. Unsupervised machine learning is typically applied to solve problems where an unknown data structure might be present in the data. As the data is unlabelled, the machine learning process is required to operate to identify implicit relationships between the data for example by deriving a clustering metric based on internally derived information. For example, an unsupervised learning technique can be used to reduce the dimensionality of a data set and attempt to identify and model relationships between clusters in the data set, and can for example generate measures of cluster membership or identify hubs or nodes in or between clusters (for example using a technique referred to as weighted correlation network analysis, which can be applied to high-dimensional data sets, or using k-means clustering to cluster data by a measure of the Euclidean distance between each datum).

Semi-supervised learning is typically applied to solve problems where there is a partially labelled data set, for example where only a subset of the data is labelled. Semi-supervised machine learning makes use of externally provided labels and objective functions as well as any implicit data relationships. When initially configuring a machine learning system, particularly when using a supervised machine learning approach, the machine learning algorithm can be provided with some training data or a set of training examples, in which each example is typically a pair of an input signal/vector and a desired output value, label (or classification) or signal. The machine learning algorithm analyses the training data and produces a generalised function that can be used with unseen data sets to produce desired output values or signals for the unseen input vectors/ signals. The user needs to decide what type of data is to be used as the training data, and to prepare a representative real-world set of data. The user must however take care to ensure that the training data contains enough information to accurately predict desired output values without providing too many features (which can result in too many dimensions being considered by the machine learning process during training and could also mean that the machine learning process does not converge to good solutions for all or specific examples). The user must also determine the desired structure of the learned or generalised function, for example whether to use support vector machines or decision trees.

The use of unsupervised or semi-supervised machine learning approaches are sometimes used when labelled data is not readily available, or where the system generates new labelled data from unknown data given some initial seed labels.

Machine learning may be performed through the use of one or more of: a non-linear hierarchical algorithm; neural network; convolutional neural network; recurrent neural network; long short-term memory network; multi-dimensional convolutional network; a memory network; fully convolutional network or a gated recurrent network allows a flexible approach when generating the predicted block of visual data. The use of an algorithm with a memory unit such as a long short-term memory network (LSTM), a memory network or a gated recurrent network can keep the state of the predicted blocks from motion compensation processes performed on the same original input frame. The use of these networks can improve computational efficiency and also improve temporal consistency in the motion compensation process across a number of frames, as the algorithm maintains some sort of state or memory of the changes in motion. This can additionally result in a reduction of error rates.

Developing a machine learning system typically consists of two stages: (1) training and (2) production. During the training the parameters of the machine learning model are iteratively changed to optimise a particular learning objective, known as the objective function or the loss. Once the model is trained, it can be used in production, where the model takes in an input and produces an output using the trained parameters.

During training stage of neural networks, verified inputs are provided, and hence it is possible to compare the neural network's calculated output to then the correct the network is need be. An error term or loss function for each node in neural network can be established, and the weights adjusted, so that future outputs are closer to an expected result. Backpropagation techniques can also be used in the training schedule for the or each neural network.

The model can be trained using backpropagation and forward pass through the network. The loss function is an objective that can be minimised, it is a measurement between the target value and the model's output.

The cross-entropy loss may be used. The cross-entropy loss is defined as $$L_{CE} = -\sum_{c=1}^{C} y * \log(s)$$

where C is the number of classes, y∈{0,1} is the binary indicator for class c, and s is the score for class c.

In the multitask learning setting, the loss will consist of multiple parts. A loss term for each task.

$$L(x) = \lambda_1 L_1 + \lambda_2 L_2$$

Where $L_1$, $L_2$ are the loss terms for two different tasks and $\lambda_1$, $\lambda_2$ are weighting terms.

Any system features as described herein may also be provided as method features, and vice versa. As used herein, means plus function features may be expressed alternatively in terms of their corresponding structure.

Any feature in one aspect may be applied to other aspects, in any appropriate combination. In particular, method aspects may be applied to system aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

The invention claimed is:

1. A computer-aided method of analysing medical images, the method comprising:
   receiving a plurality of medical images, comprising a first set of images and a second set of images;
   using one or more trained machine learning models to independently analyse said plurality of medical images to determine a malignancy output across the plurality of medical images;
   generating output data based on the determined malignancy output, wherein generating the output data comprises
      determining a first average malignancy output of the first set of images,
      determining a second average malignancy output of the second set of images, and
      determining the greater of the first average malignancy output and the second average malignancy output;
   receiving input data relating to manually determined characteristics of the one or more medical images, the manually determined characteristics determined by a first user; and
   determining a degree of similarity between the malignancy output and the manually determined characteristics, wherein, if the degree of similarity is below a predetermined threshold, an output is produced to trigger a further analysis of the plurality of medical images by a second user.

2. The method of claim 1 wherein the further analysis comprises further analysis by a computer-aided diagnosis system.

3. The method of claim 1 wherein the further analysis comprises any or any combination of:
   a computerised tomography (CT) scan;
   an ultrasound scan;
   a magnetic resonance imaging (MRI) scan;
   a tomosynthesis scan; and/or
   a biopsy.

4. The method of claim 1 wherein the plurality of medical images-comprises one or more mammographic or X-ray scans.

5. The method of claim 1 wherein the one or more trained machine learning models comprise a model selected from a non-linear hierarchical algorithm, a neural network, a convolutional neural network, a recurrent neural network, long short-term memory network, multi-dimensional convolutional network, a memory network, fully convolutional network, or a gated recurrent network.

6. The method of claim 1 wherein using one or more trained machine learning models to independently analyse said plurality of medical images to determine a malignancy output comprises segmenting one or more anatomical regions.

7. The method of claim 1 wherein the output data further comprises overlay data indicating a segmentation outline and/or a probability masks showing one or more locations of one or more segmented regions.

8. The method of claim 1 wherein using one or more trained machine learning models to independently analyse said plurality of medical images to determine a malignancy output comprises identifying tissue type and/or density category and/or identifying architectural distortion.

9. The method of claim 8 wherein the further analysis comprises one or more additional medical tests dependent upon the density category determined based on the plurality of medical images.

10. The method of claim 1 wherein using one or more trained machine learning models to independently analyse said plurality of medical images to determine a malignancy output comprises automatically identifying one or more anomalous regions in the medical image.

11. The method of claim 1 wherein using one or more trained machine learning models to independently analyse said plurality of medical images to determine a malignancy output comprises identifying and distinguishing between a malignant lesion and/or a benign lesion and/or typical lesion.

12. The method of claim 11 wherein the output data further comprises overlay data indicating a probability mask for the one or more lesions.

13. A system for analysing sets of medical images, the system comprising:
    a user terminal operable to input diagnosis metadata for at least a first set of images and a second set of images; and
    a processing unit configured to
        independently analyse at least the first set of images and the second set of images to determine a malignancy output across at least the first set of images and the second set of images,
        generate output data based on the determined malignancy output at least by determining a first average malignancy output of the first set of images, determining a second average malignancy output of the second set of images, and determining the greater of the first average malignancy output and the second average malignancy output, and
        determine a degree of similarity between the malignancy output and the diagnosis metadata, wherein, if the degree of similarity is below a predetermined threshold, produce an output to trigger a further analysis of at least the first set of images and the second set of images.

14. The system of claim 13 further comprising:
    a medical imaging device;
    a picture archiving communication system, PACS;
    an output viewer operable to display a requirement for or trigger a further analysis of at least the first set of images and the second set of images.

15. A non-transitory computer readable medium comprising instructions which, when executed by a computer, cause the computer to carry out a process for analysing medical images, the process comprising:
    receiving a plurality of medical images, comprising a first set of images and a second set of images;
    using one or more trained machine learning models to independently analyse the medical images to determine a malignancy output across the plurality of medical images;
    generating output data based on the determined malignancy output, wherein generating the output data comprises
        determining a first average malignancy output of the first set of images,
        determining a second average malignancy output of the second set of images, and
        determining the greater of the first average malignancy output and the second average malignancy output;
    receiving input data relating to manually determined characteristics of the one or more medical images;
    determining a degree of similarity between the malignancy output and the manually determined characteristics; and
    in response to the degree of similarity being below a predetermined threshold, producing an output to trigger a further analysis of the medical images.

16. The non-transitory computer readable medium of claim 15 wherein the further analysis comprises further analysis by a computer-aided diagnosis system.

17. The non-transitory computer readable medium of claim 15 wherein using one or more trained machine learning models to independently analyse said plurality of medical images to determine a malignancy output comprises segmenting one or more anatomical regions.

18. The non-transitory computer readable medium of claim 15 wherein the output data further comprises overlay data indicating a segmentation outline and/or a probability masks showing one or more locations of one or more segmented regions.

19. The non-transitory computer readable medium of claim 15 wherein using one or more trained machine learning models to independently analyse said one or more medical images to determine a malignancy output comprises identifying tissue type and/or density category and/or identifying architectural distortion.

20. The non-transitory computer readable medium of claim 19 wherein the further analysis comprises one or more additional medical tests dependent upon the density category determined based on the plurality of medical images.

* * * * *